United States Patent [19]

Williams

[11] Plant 5,176

[45] Jan. 17, 1984

[54] MINIATURE ROSE PLANT FLAMEGLO

[76] Inventor: Ernest D. Williams, 1510 Lebanon Ave., Dallas, Tex. 75208

[21] Appl. No.: 376,285

[22] Filed: May 10, 1982

[51] Int. Cl.[3] ..... A01H 5/00

[52] U.S. Cl. ..... Plt./7

[58] Field of Search ..... Plt./7

[56] References Cited

U.S. PATENT DOCUMENTS

P.P. 4,580 7/1980 Williams ..... Plt./7

P.P. 4,755 7/1981 Williams ..... Plt./7

*Primary Examiner*—James R. Feyrer

[57] ABSTRACT

The subject of the present disclosure is a new and distinct variety of miniature rose plant characterized by the very double flowers of yellow which become washed or tinted with red as they mature.

1 Drawing Figure

1

The present invention relates to a new and distinct variety of hardy, dwarf, bush type rose plant of the miniature class; the variety being primarily characterized—as to novelty—by the very double flowers of yellow which become washed or tinted with red as they mature, which in general color effect are similar to Circus, a Floribunda variety (U.S. Plant Pat. No. 1,382, expired).

The variety is further characterized by:

An abundance of bloom, with flowers usually borne singly on sturdy, slender stems.

Fragrance: slight.

A plant which is vigorous, of rounded somewhat upright shape with firm glossy, small foliage with pointed leaflets; the buds and flowers being similar in form (but with more petals) to Over The Rainbow (miniature—U.S. Plant Pat. No. 3,472).

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery, located at Dallas, Tex. under conditions of careful control and observation, as a cross between Starburst (U.S. Plant Pat. No. 2,974), as the seed parent and Over The Rainbow (miniature—U.S. Plant Pat. No. 3,472), as the pollen parent.

Subsequent to origination of the variety I successfully reproduced it, at my nursery located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; upright; seedling; greenhouse; outdoors; cut flowers; garden decoration; potted plant.

Class: Miniature.

2

*Variety name.*—Flameglo.

Flowers borne: Usually singly on slender wirey stems.

Quantity of bloom: Abundant both outside and in greenhouse.

Bud:

Peduncle.—Medium length; slender but sturdy; erect; medium green, sometimes tinted bronze (outdoors); Hairs — few or none. Before calyx breaks; size — small.

*Form.*—Ovid with some foliaceous appendages and few or no tiny hairs on surface of bud; with foliaceous parts extending beyond the tip of the bud equal to one-half or less of its length.

*Color.*—Medium green, occasionally tinted with bronze (outdoors). As calyx breaks, color — yellow. Opening: opens well in all weather.

Bloom:

*Size when fully open.*—Small — ($1\frac{1}{4}$").

*Petalage.*—Double — arranged regularly, plus several small petaloids.

*Form.*—Imbricated, with petals reflexing loosely outward and later at maturity, rolled loosely outward and downward. Open flowers usually show no stamens.

Petals: Fairly thick; satiny on inside and on outside surface.

*Shape.*—Outside petals, broad lanceolate (almost round) with rounded or acute tip; intermediate — broad lanceolate with acute tip; inside — lanceolate with acute tip.

Color: Newly opened flower from a plant grown (Spring 1982), Dallas, Tex.

*Outside petal.*—Outside surface — near Primrose Yellow 601/1 or lighter, sometimes green tint. Inside surface — near Primrose Yellow 601/1 or lighter.

*Intermediate petal.*—Outside surface — similar to outside petal, but little or no greenish tint. Inside surface — similar to outside petal.

*Inner petal.*—Outside surface — similar to intermediate petal; inside surface — similar to intermediate petal. General color effect; newly opened flower — yellow at first (near Primrose Yellow 601/1 or lighter) gradually developing a reddish overlay on petal tips. Said red overlay developing gradually, the intensity or depth of red being related to the amount of sunlight striking the flower. Only that portion of petal (top surface) exposed to sunlight becomes red. The shades of red overlay can be very light to a red color near Scarlet 19/1 (or similar — said red overlay often appears orange red due to the undertone of yellow. Three days open — color similar to newly opened flowers but yellow area becoming more tinted or overlaid with red on tips of upper surface. Behavior — opens well in all weather. Color lasts well even in hot weather. Red coloring more pronounced in full sunlight (outdoors) — more yellow and pink in greenhouse. Spent petals drop off. Flower longevity (April 1981) — Plant in pot 6–8 days or longer. Cut flowers at living room temperature 4–5 days or longer.

Reproductive organs:

*Stamens.*—Usually none.

*Filaments.*—Usually none.

*Anthers.*—None.

*Pollen.*—None.

*Pistils.*—Malformed.

*Ovaries.*—All enclosed in calyx.

*Hips.*—None.

*Sepals.*—Permanent; spear shaped; recurved against peduncle.

*Seed.*—None.

Foliage:

*Leaves.*—Compound of five (sometimes three or seven) leaflets; fairly small; leathery; glossy.

*Leaflets.*—Shape: broad, nearly oval; apex acute; base rounded. Margin serrate. Color: Dark green; new growth — normal (medium-green). Rachis: Medium strength; upper side may have a few tiny short prickles or hairs, grooved. Underside — several small hooked thorns with few or no tiny prickles. Stipules: Medium long; narrow to medium width medium length; narrow points which turn out usually at about 45 degrees or more.

Growth:

*Habit.*—Dwarf; bushy; upright; much branched.

*Growth.*—Free vigorous; internodes short.

*Canes.*—Medium; slender; sturdy.

*Main stems.*—Color: Medium green.

*thorns.*—Average; slender; nearly straight, inclined slightly downward; color — brown (tan). Prickles — none. Hairs — none.

*Branches.*—Color: Medium green. Thorns: Moderate number; medium length; slender; nearly straight, inclined downward. Medium oval base. Prickles: None. Hairs — None.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy; dwarf; bushy; upright; much branched habit, substantially as illustrated and described, characterized by buds and flowers of medium yellow, with red or pinkish tint or overlay on petal tips as flowers mature, the bud and flower resembling the variety Circus (U.S. Plant Pat. No. 1,382, expired) in color and resembling the variety Over The Rainbow in form and size; and further characterized by a plant of vigorous and compact growth habit, easy to propagate from cuttings, with an abundance of small to medium size glossy foliage and an abundance of flowers borne usually singly on sturdy wirey stems.

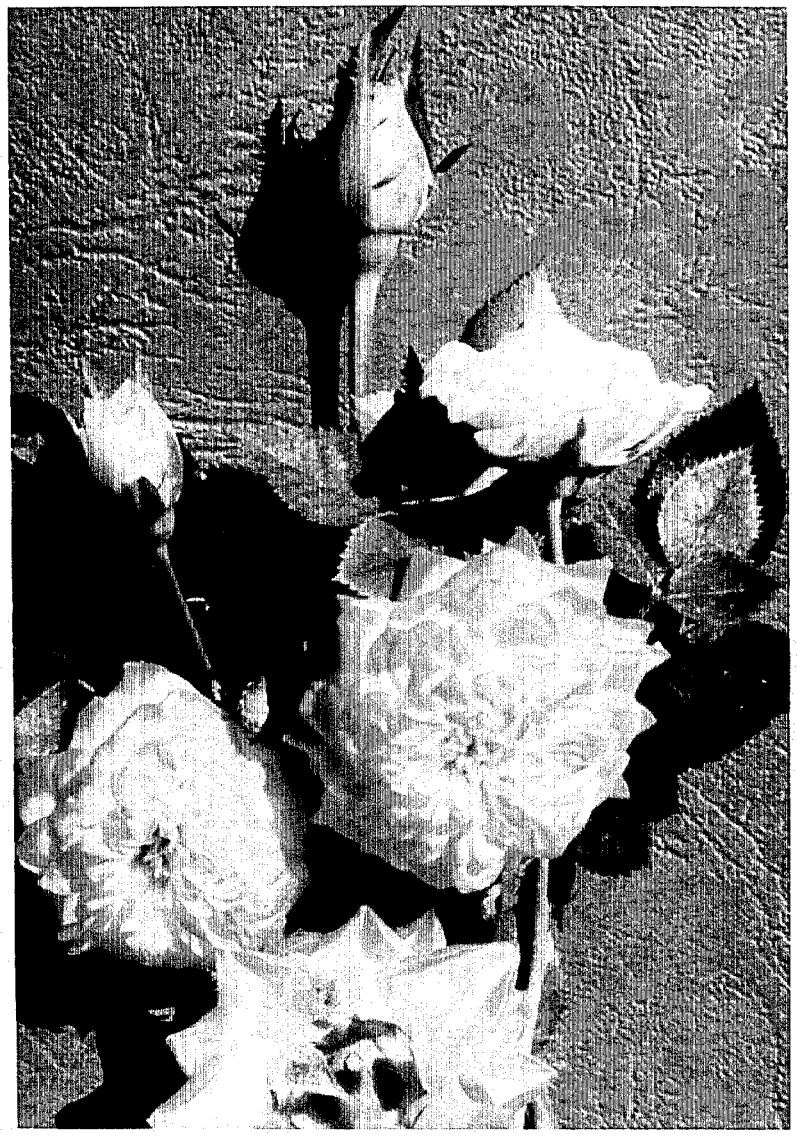

* * * * *